United States Patent
Gunz et al.

[11] Patent Number: 5,315,099
[45] Date of Patent: May 24, 1994

[54] GLARE SHIELDING DEVICE AND PROCESS FOR OPERATING SAME

[75] Inventors: Stefan Gunz, Wädenswil; Livio Ghisleni, Wilen, both of Switzerland

[73] Assignee: Xelux AG, Switzerland

[21] Appl. No.: 995,145

[22] Filed: Dec. 22, 1992

[30] Foreign Application Priority Data

Dec. 31, 1991 [CH] Switzerland ............... 03866/91

[51] Int. Cl.⁵ .............................................. G01J 1/20
[52] U.S. Cl. ................................. 250/201.1; 359/63
[58] Field of Search ......... 250/201.1, 214 VT, 214 LA; 359/63, 66, 68, 72, 74, 85, 228

[56] References Cited

U.S. PATENT DOCUMENTS 4,240,709 12/1980 Hornell ............................... 359/63
4,701,021 10/1987 Le Pesant et al. ................. 359/228

Primary Examiner—David C. Nelms
Assistant Examiner—K. Shami
Attorney, Agent, or Firm—Wigman, Cohen, Leitner & Myers

[57] ABSTRACT

An electro-optical glare shielding device for protective glasses, protective helmets or protective masks, which includes an electro-optical glare shield including at least one liquid crystal cell, an electronic circuit connected to the electro-optical glare shield for applying an electric operating voltage thereto for varying the optical transmission value of the at least one liquid crystal cell, a light sensor connected to the electronic circuit for providing an input signal thereto indicative of sensed light adjacent to the electro-optical glare shielding device and in which the electronic circuit produces an electric operating voltage such that the optical transmission value of the at least one liquid crystal cell is less than 1% and the electric operating voltage frequency is less than 32 Hertz.

20 Claims, 2 Drawing Sheets

GLARE SHIELDING DEVICE AND PROCESS FOR OPERATING SAME

BACKGROUND OF THE INVENTION

The present invention relates to a process for operating an electro-optical glare shielding device and a glare shielding device suitable for implementing this process.

Glare shielding devices are universally known and are used preferably in the welding and cutting torch technology. As a rule, with these glare shielding devices the radiation above 780 nm (infrared) and below 365 nm (ultraviolet) are filtered and only the radiation in the visible range is dimmed.

Safety shields are known, for example, from French Patent No. FR-2 293 188, where, in particular, safety shields are described that are constructed of an ultraviolet light filter, an infrared filter, a polarizer and an analyzer, between which is an electro-optical element. The electro-optical element rotates the polarizing direction of the light polarized by the polarizer into a direction for which the analyzer is opaque. Thus, within a few tenths of a second adequate dimness can be obtained. During this dimming period, however, the user is intensively blinded and is thus inadequately protected.

Therefore, electronic circuits, as described for example in U.S. Pat. No. 3,575,491, have already been developed to operate liquid crystal cells, with which the change-over times of the liquid crystal cells are in the millisecond range. To this end, a high electric voltage, which fluctuates with a frequency of over 60 Hertz, is attached to the liquid crystal cell. Unfortunately the operation of these devices is associated with a high electric power and thus the properties of the liquid crystal cells that are used are rapidly modified.

These and all other prior art glare shielding devices are characterized by a high power consumption. Additionally, the drawbacks of devices with unstable or rapidly consumed voltage sources are well known.

Since today's conventional glare shielding devices utilize a plurality of liquid crystal cells, usually several connected in series, in the steepest range of the transmission characteristic of these liquid crystal cells, the high temperature dependence and the high voltage dependence of this characteristic have a high negative effect. In particular, during normal operation these dependencies render the use of automatically starting glare shielding devices difficult and make it necessary to compensate for these changes in transmission.

Another problem that has still remained unsolved relates to the scattered light which is produced by the liquid crystal cells themselves and cannot be eliminated by the polarizers.

OBJECTS AND SUMMARY OF THE INVENTION

A primary object of the present invention is to provide reliable, simple, and easy-to-service light glare shields. Another object of the present invention is to provide a glare shielding device, which does not exhibit the drawbacks of the known devices; and in particular an automatic glare shield is to be operated in such a manner that the glare shield exhibits a low power consumption, operates so as to be in essence temperature insensitive and generates little scattered light of its own.

The process according to the present invention is characterized in essence by the fact that at least one liquid crystal cell is used to construct the glare shield and is operated in a voltage range in which the optical transmission of this liquid crystal cell, i.e. without infrared and/or ultraviolet filter put in the circuit, exhibits a value between 0.01% and 1%. Normally this is achieved at a voltage ranging from 5-20 volts. Commercial range crystal cells are normally operated in their transmission range between 10% to 90%, i.e. at a voltage of 1-4 volts.

According to the present invention, an alternating current, whose frequency is in the range of 0.1 Hertz, is applied to this liquid crystal cell. In this manner the power consumption can be significantly decreased as compared to conventional glare shielding devices.

Operating the liquid crystal cell at 0.1 Hertz is preferred because just the slightest change in brightness in the range of 1-20 Hertz is perceived by the eye as an unpleasant flickering. A pulse-like change in brightness at 0.1 Hertz is, however, no longer found to be disturbing.

By operating the liquid crystal cell in the range of a higher electric voltage, it is only slightly sensitive to the displacements of the transmission characteristic, as can be caused, for example, by temperature fluctuations or instabilities of the voltage sources. Another advantage arising from operating the liquid crystal cell according to the invention follows from a significant reduction in scattered light, as shown by every liquid crystal cell upon application of high voltages. In addition, the operating method according to this invention results in the fact that the switch change-over generated by the alternating current generates a hardly visible penetration of brightness, as compared to the typical operation in the transmission range between 10% and 90%. Thus, the present glare shielding device exhibits not only significantly less power consumption, but also reduces the frequency and intensity of the alternating current-induced penetration of brightness and thus the risk with respect to known eye irritations or injuries.

At this point it must also be noted that modern welding and cutting devices generate pulse-like light emissions, preferably in the range between 1-200 Hertz. With the process according to the invention even undesired interferences between the operating frequency of the glare shielding device and the working frequency of the above devices can be eliminated.

An electronic circuit that is suitable for implementing the process of the invention exhibits at least one light sensor, a threshold switch, a rapid starting circuit, an oscillator, a liquid crystal cell driver, a liquid crystal cell and an adapted power supply.

In a preferred embodiment, solar cells are used for the power supply. Thus, the ease with which the glare shielding device of the invention can be serviced is further increased.

In another embodiment of the circuit according to the present invention a memory is provided, preferably having a flip-flop circuit. This memory guarantees an alternatingly polarized starting voltage even when the glare shielding device is operated for a short period of time.

BRIEF DESCRIPTION OF THE DRAWINGS

The present invention will be explained in detail with reference to the drawings, wherein.

DETAILED DESCRIPTION OF A PREFERRED EMBODIMENT

Figure 1:
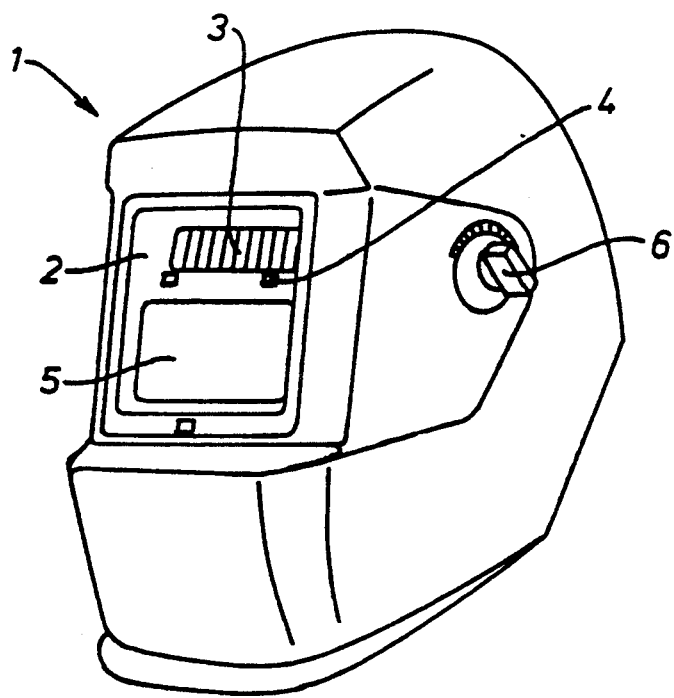
FIG. 1 show, in perspective, a protective mask with a glare shielding device according to the present invention.

FIG. 1 shows a glare protective mask 1 with a glare shielding device 2, as currently used. Glare shielding device 2 is designed as a cassette and can be rapidly reliably interchanged. The side of cassette 2 facing the light source to be dimmed includes a plurality of solar cells 3, at least one photosensor 4 and a safety shield 5. Safety shield 5 comprises several elements layered by conventional methods. Safety shield 5 comprises, in a simple embodiment: a first polarizer, which is provided with a scratch resistant layer and which simultaneously also acts as an ultraviolet filter; an infrared filter; at least one liquid crystal cell; a second polarizer, which is also provided with a scratch resistant layer; and a magnifying lens. In this embodiment the dimming can be manually controlled by knob 6.

Figure 2:
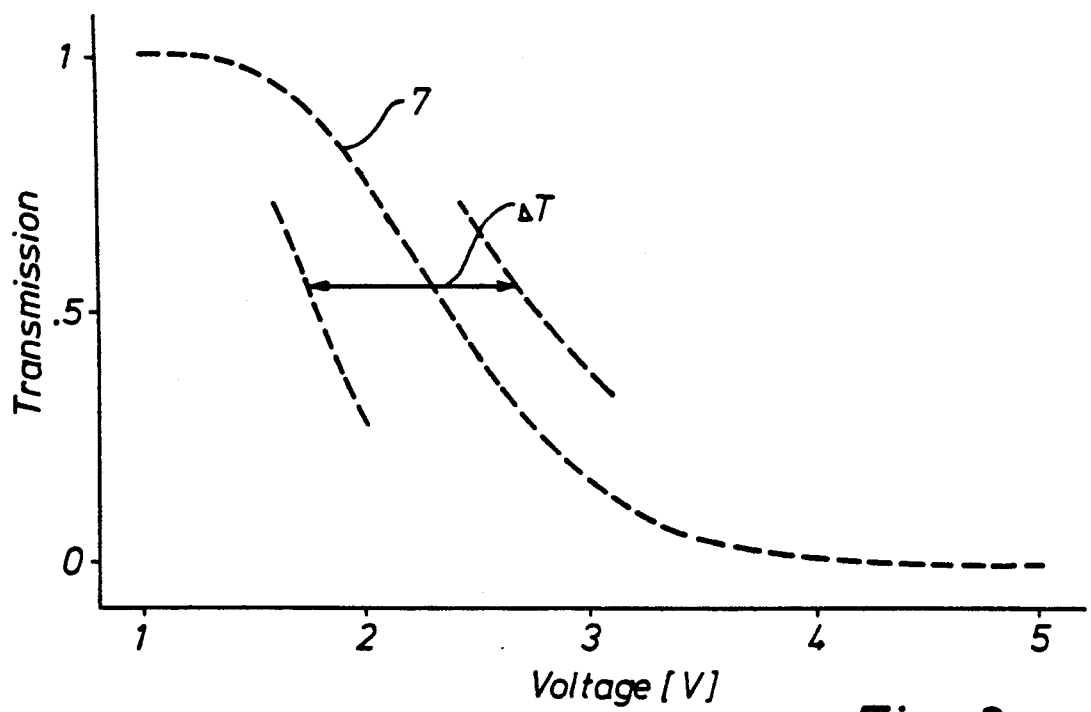
FIG. 2 is a graph which shows a transmission characteristic of a commercial liquid crystal cell.

Referring to graph illustrated in FIG. 2, a transmission characteristic 7 that is typical for a commercial twisted nematic liquid crystal display (TN-LCD) is shown as a function of voltage V. This characteristic makes it clear that these liquid crystal cells are totally light transparent at low voltages and are opaque in the range of 1-4 volts. For voltages above 4 volts the transmission at this liquid crystal cell is less than 1%. Transmission values of less than 1% are, however, mandatory precisely for the present application. Thus the liquid crystal cells used in service consume a disproportionately large amount of current, especially when high extinction, i.e. of more than 99%, is to be obtained. Therefore, several liquid crystal cells are usually connected in series. In this manner, the problem is ameliorated, but is not satisfactorily solved.

In contrast, in the present invention this effect can be obtained with only one liquid crystal cell. According to the invention, a commercially available liquid crystal cell is operated at an unusually low alternating frequency, i.e. approximately 0.1 Hertz. In this manner, the output required by the normally necessary reversal of poles of the liquid crystal cells can be reduced and the increase in performance from the relatively high operating voltage can be surprisingly well compensated for. It is obvious that suitable liquid crystal cells according to the invention can also be operated with d.c. current. In fact, the increase in performance from the operating voltage according to the invention is less than the saving resulting from the low operating frequency.

At the same time a reduction in the scattered light generated by the liquid crystal cells is obtained due to the increased voltage. In addition, the penetration of brightness during the change over process is less, since with the increased voltage even the liquid crystal cell dims more rapidly.

Under the conditions of the invention the suitably designed liquid crystal cells and in particular liquid crystal cells that can be operated at low frequency will function flawlessly for several years.

The transmission characteristic in FIG. 2 is displaced as the temperature changes. In so doing, a change of approximately 20° C. can result in transmission displacements of up to 50%. When the liquid crystal cells are operated according to the invention, this displacement is hardly noticeable and, therefore, also causes no changes in the transmission.

Figure 3:
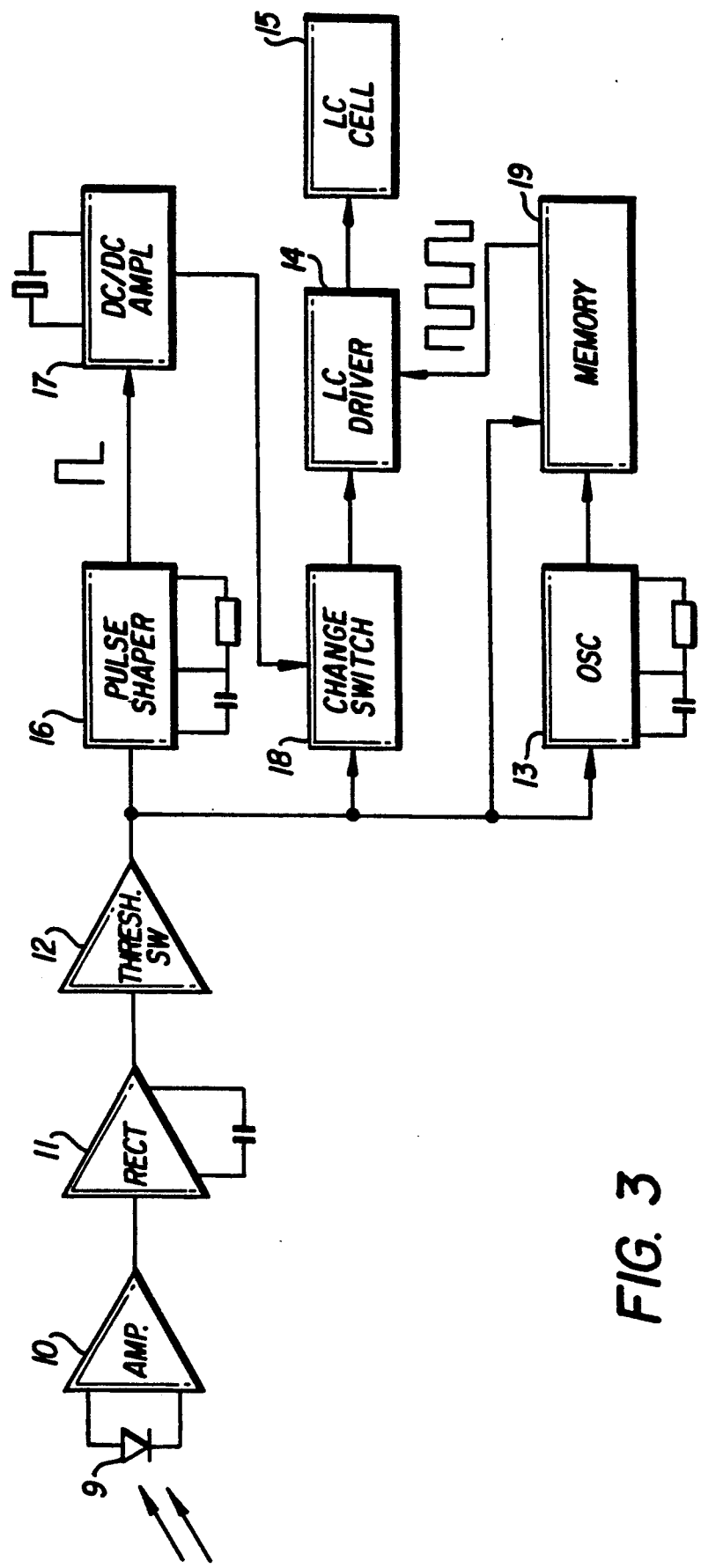
FIG. 3 is a block diagram for an electronic circuit according to the present invention.

FIG. 3 shows a block diagram of an electronic circuit, suitable to implement the process of the present invention. The signal generated by a photodetector 9 is amplified and rectified by circuits 10 and 11 and fed to a threshold switch 12. The signal generated by this threshold switch 12 is fed to an oscillator 13, which is provided with a divider and which generates the alternating frequency for an LCD driver 14, to which a liquid crystal cell 15 is attached. To increase the switching speed the signal generated by the threshold switch 12 is also fed to a pulse shaper 26 and a DC/DC voltage amplifier 17, which provide the trip-on signal of the threshold switch 12 with a sharp starting edge. This signal is fed to a change-over switch 18, in order to increase the operating voltage, for example 6-12 volts, for the circuit closing, suddenly, for example, to 15-30 volts and in order to switch it back again to the normal operating voltage after a specified time, for example 1-20 ms.

In a preferred embodiment a memory 19 is connected between the oscillator 13 and the LCD driver 14. This memory ensures that the polarity of the starting voltage is changed at every circuit closing, in particular in order to reduce electrolytic wear phenomena at the liquid crystal cell 15.

It is noted that the specific construction of both the glare shield and also the electronic circuit is within the average skill of the expert. In particular, instead of photodetectors, electromagnetic or pyroelectric detectors can also be used, or the solar cells can also be an integrating component of the glare shield, or the electronic circuit can also be adjustable by hand. In particular the choice of an especially suitable liquid crystal cell is within the normal engineering capacity of a person skilled in the art.

Embodiments of the means suitable for implementing the process according to the invention, in particular optical coatings of individual elements of the electro-optical glare shield, or specific designs of the liquid crystal cell, in particular corrosion resistant layers for their electrodes are also within the average skill of the expert.

The use of the glare shield according to the invention and its electronic circuit in glasses of any kind, e.g.; designer glasses, protective sun glasses, disco glasses, glasses for car drivers and pilots is also contemplated.

Although only preferred embodiments are specifically illustrated and described herein, it will be appreciated that many modifications and variations of the present invention are possible in light of the above teachings and within the purview of the appended claims without departing from the spirit and intended scope of the invention.

We claim:

1. An electro-optical glare shielding device for protective glasses, protective helmets, or protective masks, comprising:

an electro-optical glare shield including at least one liquid crystal cell;

an electronic circuit connected to said electro-optical glare shield for applying an electric operating voltage thereto for varying an optical transmission value of said at least one liquid crystal cell; and a light sensor connected to said electronic circuit for providing an input signal thereto indicative of sensed light adjacent to said electro-optical glare shielding device;

wherein said at least one liquid crystal cell includes means for extending liquid crystal cell service life comprising at least one corrosion resistant layer and at least one of a corrosion-neutral liquid and corrosion-inhibiting additives, and wherein said electronic circuit produces an electric operating voltage such that the optical transmission value of said at least one liquid crystal cell is less than about 1% and said electric operating voltage has a frequency of less than about 32 Hertz.

2. The electro-optical glare shielding device of claim 1, wherein said electric operating voltage frequency is about 0.1 Hertz.

3. The electro-optical glare shielding device of claim 1, wherein said electronic circuit comprises:
   an amplifier connected to said light sensor for amplifying said input signal received from said light sensor;
   a rectifier for receiving said amplified signal for producing a rectified signal;
   threshold switch means connected to said rectifier for generating a trip-on signal upon receiving said rectified signal; and
   oscillator means connected to receive said trip-on signal and to generate an alternating voltage signal in response thereto which alternating voltage signal is fed to an LCD driver for driving said at least one liquid crystal cell.

4. The electro-optical glare shielding device of claim 3, wherein said electronic circuit further includes circuit means connected to receive said trip-on signal and to produce an accelerating signal for quickly generating said trip-on signal.

5. The electro-optical glare shielding device of claim 1, wherein said at least one liquid crystal cell operates using direct current voltage.

6. The electro-optical glare shielding device of claim 3, wherein said electronic circuit oscillator means clocks said LCD driver at a frequency of less than about 32 Hertz such that said LCD driver produces an operating voltage which produces said about 1% optical transmission value in said at least one liquid crystal cell.

7. The electro-optical glare shielding device of claim 6, wherein said electric operating frequency is about 0.1 Hertz.

8. The electro-optical glare shielding device of claim 6, wherein said electronic circuit includes a memory having a flip-flop circuit for producing an alternatingly polarized starting voltage which is fed to said LCD driver.

9. A process for operating an electro-optical glare shielding device including at least one liquid crystal cell for protective glasses, protective helmets or protective masks, comprising the steps of:

sensing a light event adjacent to said electro-optical glare shielding device and generating an input signal in response to said sensed light event;

setting an optical transmission value of said at least one liquid crystal cell in response to said input signal; and generating an operating voltage having a frequency of less than about 32 Hertz using said electronic circuit for operating said at least one liquid crystal cell at about 1% optical transmission value.

10. The process for operating an electro-optical glare shielding device of claim 9, wherein said operating voltage frequency is about 0.1 Hertz.

11. The process for operating an electro-optical glare shielding device of claim 9, wherein said at least one liquid crystal cell is operated with direct current.

12. The process for operating an electro-optical glare shielding device of claim 9, wherein said step of setting an optical transmission value of said at least one liquid crystal cell comprises the steps of:
   amplifying and rectifying said input signal generated by sensing a light event adjacent to said electro-optical glare shielding device;
   generating a trip-on signal in response to said amplified and rectified input signal;
   generating an alternating voltage signal for driving an LCD driver circuit using said trip-on signal; and
   driving said at least one liquid crystal cell using said generated alternating voltage signal.

13. The process for operating an electro-optical glare shielding device of claim 12, wherein said generated alternating voltage signal is an alternatingly polarized starting voltage signal.

14. The process for operating an electro-optical glare shielding device of claim 12, further including the step of accelerating said generating of said trip-on signal.

15. The process for operating an electro-optical glare shielding device of claim 12, wherein said operating voltage frequency is about 0.1 Hertz.

16. The process for operating an electro-optical glare shielding device of claim 13, wherein said operating voltage frequency is about 0.1 Hertz.

17. The process for operating an electro-optical glare shielding device of claim 14, wherein said operating voltage frequency is about 0.1 Hertz.

18. The electro-optical glare shielding device of claim 3, wherein said alternating voltage signal is a step change voltage having a range of from about 15 to about 30 volts, and a period of said step change from about 1 to about 20 milliseconds.

19. The electro-optical glare shielding device of claim 1, wherein said threshold switch means for generating includes a DC/DC amplifier.

20. The process for operating an electro-optical glare shielding device of claim 12, wherein said generated alternating voltage signal is from about 15 to about 30 volts and said liquid crystal cell is driven by said alternating voltage signal for a period of from about 1 to about 20 milliseconds.

* * * * *